United States Patent [19]
Ehlers et al.

[11] 4,379,137
[45] Apr. 5, 1983

[54] DISINFECTING AND PRESERVING COMPOSITION COMPRISING A SYNERGISTIC COMBINATION OF A POLYMERIC QUATERNARY AMMONIUM COMPOUND AND A 3-ISOTHIAZOLONE COMPOUND

[75] Inventors: Helmut H. Ehlers; Heinz Eggensperger, both of Hamburg; Lothar Bücklers, Norderstedt; Ulrich Eigener, Henstedt-Ulzburg; Karl-Heinz Diehl, Norderstedt; Norbert Weigand, Reutlingen, all of Fed. Rep. of Germany

[73] Assignee: Sterling Drug Inc., New York, N.Y.

[21] Appl. No.: 172,571

[22] Filed: Jul. 28, 1980

[30] Foreign Application Priority Data
Jun. 30, 1979 [DE] Fed. Rep. of Germany ....... 2930865

[51] Int. Cl.³ .................... A01N 33/12; A01N 43/78
[52] U.S. Cl. .................................... 424/78; 424/270; 424/329
[58] Field of Search .................... 424/78, 329, 270

[56] References Cited
U.S. PATENT DOCUMENTS

| 3,517,022 | 6/1970 | Miller et al. | 260/304 |
| 3,761,488 | 9/1973 | Lewis et al. | |
| 3,870,795 | 3/1975 | Miller et al. | 424/220 |
| 3,874,870 | 4/1975 | Green et al. | 424/78 |
| 3,931,319 | 1/1976 | Green et al. | 424/244 |
| 4,025,627 | 5/1977 | Green et al. | 424/248.4 |
| 4,027,020 | 5/1977 | Green et al. | 424/248.56 |
| 4,325,201 | 4/1982 | Lewis et al. | |

FOREIGN PATENT DOCUMENTS
1036070 8/1978 Canada .

Primary Examiner—Allen J. Robinson
Attorney, Agent, or Firm—Frederik W. Stonner; B. Woodrow Wyatt; Paul E. Dupont

[57] ABSTRACT

The invention is a synergistic disinfecting and preserving composition comprising in admixture a polymeric quaternary ammonium compound and a 3-isothiazolone derivative, and a method of use thereof, for protecting aqueous systems against contamination by deleterious microorganisms.

2 Claims, No Drawings

DISINFECTING AND PRESERVING COMPOSITION COMPRISING A SYNERGISTIC COMBINATION OF A POLYMERIC QUATERNARY AMMONIUM COMPOUND AND A 3-ISOTHIAZOLONE COMPOUND

BACKGROUND OF THE INVENTION

1. Field of the Invention

The invention relates to disinfecting and preservative compositions which are particularly suited as disinfectants and preservatives for aqueous systems including those used in air conditioning, humidifying and cooling water systems.

2. The Prior Art

In hospital operating theaters, appropriate humidity must be maintained for reasons of safety. This can be achieved by steam humidification or circulation humidification. In circulation humidification, water in so-called "wash chambers" is circulated by pump and sprayed through fine nozzles. In order to prevent and combat transmission of infectious microorganisms by such air conditioning systems, the water employed must be treated so as to prevent the growth therein of microorganisms.

Although a number of antimicrobial additives for the wash chambers in humidification systems is known, they all suffer some kind of disadvantage and fail to meet certain important prerequisites so that the problem of preventing transmission of infectious microorganisms, which is so important in surgery, has not been satisfactorily resolved. The prerequisites a disinfecting and preserving agent for humidification systems should have are as follows:

1. broad spectrum of antimicrobial activity at low concentrations and low temperatures.
2. stability against shearing forces and oxidation.
3. low toxicity, especially inhalation toxicity.
4. no undue foaming in use.
5. essentially no odor.

Since foaming in systems where water is pumped and in air conditioning equipment, in whch foam particles may be carried into air conditioning ducts, is very troublesome, a disinfecting agent used in such systems should not cause foaming. Thus, the commonly employed quaternary ammonium compounds cannot be used because they cause heavy foaming.

Furthermore, the disinfecting agent used should have the lowest possible vapor pressure so that it will not evaporate from the aqueous system and reach room air. Therefore, well known disinfectants such as the lower aldehydes, e.g., formaldehyde, cannot be used.

Other well known disinfectants such as the higher alcohols and substituted phenols also cannot be used in air conditioning systems because they all have more or less pronounced odors.

Canadian Pat. No. 1,036,070 describes synergistic bactericidal compositions useful in surface disinfection, particularly surfaces soiled with organic matter, which comprises a 3-isothiazolone, a strong acid salt of a 3-isothiazolone, or a metal salt complex of a 3-isothiazolone and a bactericidal quaternary ammonium compound.

U.S. Pat. No. 3,870,795 describes certain 3-isothiazolones and metal salt complexes thereof and the use of solutions of the metal salt complexes as watercooling system microbiocides, U.S. Pat. Nos. 3,517,022 and 3,870,795 describe certain benzoisothiazolones useful as microbiocides in aqueous systems.

U.S. Pat. Nos. 3,874,870 and 4,025,627 describe certain polymeric quaternary ammonium compounds which exhibit no undue foaming and are useful as microbiocidal agents in aqueous systems.

U.S. Pat. Nos. 3,931,319 and 4,027,020 describe certain polymeric quaternary ammonium compounds which are useful as microbiocidal agents.

SUMMARY OF THE INVENTION

It has now been discovered that by combining certain polymeric quaternary ammonium compounds with certain 3-isothiazolone derivatives, a preserving and disinfecting agent is obtained which not only meets all the hereinbefore defined prerequisites for disinfectants for water circulation systems and for wash chambers of air conditioning systems but which also exhibits synergistic antimicrobial activity, i.e., the activity of the mixture is greater than the combined individual activity of the polymeric quaternary compound and the 3-isothiazolone derivative.

Thus in a composition aspect of the invention there is provided a disinfecting and preserving composition which comprises in admixture (a) a compound selected from the group consisting of polymeric quaternary ammonium compounds having the formulas:

$$R^5-\underset{\underset{R^4}{|}}{\overset{\overset{R^3}{|}}{N^\oplus}}-CH_2-A-CH_2-\left[\underset{\underset{R^2}{|}}{\overset{\overset{R^1}{|}}{N^\oplus}}-Z-\underset{\underset{R^2}{|}}{\overset{\overset{R^1}{|}}{N^\oplus}}-CH_2-A-CH_2-\right]_n\underset{\underset{R^4}{|}}{\overset{\overset{R^3}{|}}{N}}-R^5 \cdot (2n+2)X^- \text{ and} \qquad I$$

$$\left[\underset{\underset{R^2}{|}}{\overset{\overset{R^1}{|}}{N^\oplus}}-Z-\underset{\underset{R^2}{|}}{\overset{\overset{R^1}{|}}{N^\oplus}}-CH_2-A-CH_2\right]_n \cdot 2nX^- \qquad II$$

wherein $R^1$ and $R^2$, which can be the same or different, are alkyl having from 1 to 20 carbon atoms and having from 0 to 1 hydroxyl substituent, benzyl, benzyl bearing on the benzene moiety one alkyl having from 2 to 20 carbon atoms; $R^3$, $R^4$ and $R^5$, which can be the same or different, are alkyl having from 1 to 20 carbon atoms and having from 0 to 1 hydroxyl substituent, or $R^3$ and $R^4$ taken together with the nitrogen to which they are attached form a saturated heterocyclic ring having from 5 to 7 ring atoms; Z and A, which can be the same or different, are divalent alkylene radicals of 2 to 10 carbon atoms interrupted by from 0 to 1 oxygen atom and containing from 0 to 2 ethylenic double bonds; n is a whole number from 2 to 30; and X is a halogen; and (b) a 3-isothiazolone having the formula:

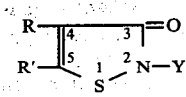
III wherein Y is alkyl having from 1 to 18 carbon atoms, cyclohexyl, phenyl, halophenyl, benzyl or halobenzyl, R and R', which can be the same or different, are hydrogen, halogen, alkyl having from 1 to 6 carbon atoms, alkenyl of 2 to 6 carbon atoms or phenyl, or R and R' together with the carbon atoms to which they are attached form a benzene ring, or a salt thereof with a strong acid, or a 3-isothiazolone metal salt complex having the formula

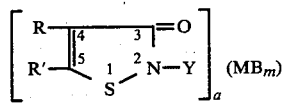
IV wherein Y, R and R' are as defined above, M is a cation of calcium or magnesium, B is a chloride anion or nitrate anion, a is the whole number 1 or 2, and m is the number 2; wherein the ratio of component (a) to component (b) is from 1:200 to 200:1.

In a method aspect of the invention there is provided a method of protecting an aqueous system which is susceptible to contamination by deleterious microorganisms from contamination by said microorganisms wich comprises treating the aqueous system with an antimicrobially effective amount of the above-defined disinfecting and preserving composition.

DETAILED DESCRIPTION INCLUSIVE OF THE PREFERRED EMBODIMENTS

The term alkyl as used herein is intended to include straight and branched alkyl.

The term halogen as represented by X herein is intended to include bromine, chlorine and iodine.

The terms halophenyl and halobenzyl as used herein include such substituents bearing on the benzene ring thereof one or more halogen atoms selected from bromine, chlorine, fluorine and iodine. When more than one halogen atom is present, they can be the same or different and can occur in any position relative to each other.

As used herein, "a saturated heterocyclic ring having from 5 to 7 ring atoms" includes, 1-pyrrolidyl, 1-piperidyl, 1-homopiperidyl, 1-piperazinyl, 4-morpholinyl and the like.

The strong acid salts of the 3-isothiazolones of formula III which can be employed include salts with hydrochloric acid, hydrobromic acid, perchloric acid, nitric acid, sulfuric acid, oxalic acid, trichloroacetic acid, p-toluenesulfonic acid, and the like.

The polymeric quaternary ammonium compounds of formulas I and II above belong to a well known class of compounds which together with methods for their preparation are described in U.S. Pat. Nos. 3,874,870, 3,931,319, 4,025,627 and 4,027,020. Thus the polymeric quaternary ammonium compounds of formula II are prepared by reaction of equimolar amounts of a diamine of the formula $R^1R^2N$—Z—$NR^1R^2$ with a dihalo compound of the formula $XCH_2$—A—$CH_2X$ where Z, $R^1$, $R^2$, A and X are as defined hereinabove. When a small excess of the dihalo compound is employed there results a polymeric quaternary compound whose termini at both ends is halogen, reaction of which with an amine of the formula $NR^3R^4R^5$, where $R^3$, $R^4$ and $R^5$ are as defined hereinabove, yields the quaternary ammonium compound of formula I.

The 3-isothiazolones of formula III and metal salt complexes of 3-isothiazolones of formula IV belong to classes of well known compounds which together with methods for their preparation are described in U.S. Pat. Nos. 3,517,022 and 3,870,795.

Polymeric quaternary ammonium compounds which can be employed in the composition of the invention include, for example, the product obtained by reaction of 1,2-dichloro-2-butene with 1,4-bis(dimethylamino)-2-butene and tris(2-hydroxyethyl)amine having the formula:

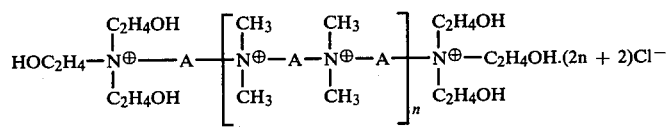
V where A is —$CH_2CH$=$CH$—$CH_2$— and n is 2 to 30; and a compound having the formula:

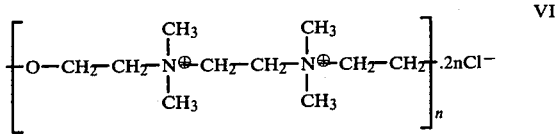
VI where n is 12 to 16 and where the molecular weight of the compound is from 3300–4400.

The composition of the invention contains the polymeric quaternary ammonium compound and the 3-isothiazolone or 3-isothiazolone metal salt complex in the ratio of from 200:1 to 1:200, and preferably in the ratio of from 100:1 to 1:1.

Mixtures of the polymeric quaternary ammonium compounds and mixtures of the 3-isothiazolones also can be used in the instant composition.

When the synergistic composition of the invention is employed in aqueous systems such as those present in air humidification equipment, the bacteriostatic component of the composition ensures that no undesirable microbial growth and hence no propagation of microorganisms occurs, even during temporary shut down of such equipment, and during subsequent normal use of such equipment the bactericidal component of the composition kills any microorganisms which possibly may be present.

The composition of the invention can be formulated as solutions in water. Although the weight percent of the instant composition in the formulated solution can vary over a wide range, the solutions can be conveniently formulated so as to contain from about 15 to 30% by weight of the composition based on the total weight of the composition and the water. In formulating the solutions other solvents which are water-miscible, such as ethyl alcohol, propyl alcohol, isopropyl alcohol and the like, may be employed in order to aid in solubilizing the active components. Furthermore, various other conventional additives may be employed such as hardness-stabilizing agents, corrosion inhibitors, pH regulating agents, suitable surfactants as emulsifying agents, etc.

The hardness stabilizing agents which can be used include 2-phosphono-1,2,4-butanetricarboxylic acid having the structural formula

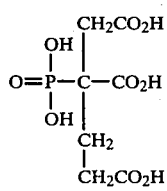

$$\begin{array}{c} \text{CH}_2\text{CO}_2\text{H} \\ \text{OH} \quad | \\ | \quad \\ \text{O}=\text{P}-\text{C}-\text{CO}_2\text{H} \\ | \quad | \\ \text{OH} \quad \\ \text{CH}_2 \\ | \\ \text{CH}_2\text{CO}_2\text{H} \end{array} \qquad \text{VII}$$

and other complex-forming carboxylic acid compounds and their sodium salts and polycarboxylic acids and their salts. The hardness stabilizing additive prevents precipitation of the active components in the treated aqueous systems which may occur due to water hardness and hence prevents scale formation between normal cleaning cycles. The hardness stabilizing additives are compatible with the composition of the invention, i.e., they do not reduce the microbiocidal activity of the instant compositions.

The composition of the invention can be used to protect a variety of aqueous systems, including those of the recirculated type, such as aqueous systems used in cooling towers, humidifiers, air conditioners, etc. They are particularly adapted for use in circulating cooling water systems and in aqueous systems used in the wash chambers of air humidification equipment.

In utilizing the composition of the invention, an antimicrobially effective amount thereof, i.e., of the combined polymeric quaternary ammonium compound and the 3-isothiazolone derivative, should be present in the aqueous system. Although the amount to be employed will vary depending on the type of aqueous system to be treated as well as on other factors such as the potential for microbial comtamination of the aqueous system, generally the composition of the invention is dissolved in the aqueous system in an amount of about 0.005 to 0.2% by weight.

Two aqueous formulations, designated Formulations 4 and 5 in Table 1 below, were prepared from compositions of the invention containing different ratios of polymeric quaternary compounds and 3-isothiazolones. In addition, there were prepared for comparison purposes three formulations, designated Formulations 1, 2 and 3 in Table 1 below, corresponding to either Formulation 4 or Formulation 5 except that either the quaternary ammonium compound or the mixture of 3-isothiazolones was omitted.

TABLE 1

| Ingredient | Formulation[a] | | | | |
|---|---|---|---|---|---|
| | 1 | 2 | 3 | 4 | 5 |
| Polymeric quaternary ammonium compound of Formula V[b] | 10.0 | — | — | 10.0 | 10.0 |
| Mixture of | | | | | |

TABLE 1-continued

| Ingredient | Formulation[a] | | | | |
|---|---|---|---|---|---|
| | 1 | 2 | 3 | 4 | 5 |
| 5-chloro-2-methyl-3-isothiazolone (10.1 parts) and 2-methyl-3-isothiazolone (3.8 parts) | — | 10.0 | 5.0 | 10.0 | 5.0 |
| 2-Phosphono-1,2,4-butane-tricarboxylic acid | 4.0 | 4.0 | 4.0 | 4.0 | 4.0 |
| 1,2,3-Benzotriazole[c] | 0.2 | 0.2 | 0.2 | 0.2 | 0.2 |
| Phosphonic acid[d] | 2.0 | 2.0 | 2.0 | 2.0 | 2.0 |
| Triethanolamine[d] | 1.55 | 1.55 | 1.55 | 1.55 | 1.55 |
| Isopropyl alcohol[e] | 10.0 | 10.0 | 10.0 | 10.0 | 10.0 |
| PEG-60 glyceryl stearate[f] | 0.1 | 0.1 | 0.1 | 0.1 | 0.1 |
| Water | 72.15 | 72.15 | 77.15 | 62.15 | 67.15 |

[a]Amounts of ingredients in percent by weight
[b]Mixture of polymers where n ranges from 2 to 30
[c]Corrosion inhibitor
[d]pH Regulator
[e]Solubilizer
[f]Polyethylene glycol (60) glyceryl monostearate; emulsifier The synergistic activity of the composition of the invention can be seen from the microbiological test results for Formulations 4 and 5 compared to those for Formulations 1-3 as presented in Tables 2-8 hereinbelow. Microbiological activity was determined in the suspension test as well as by ascertaining MIC values in series dilution tests. Bactericidal activity is determined in the suspension test and bacteriostatic activity is determined in the series dilution test. The results of the suspension test are recorded in Tables 2-6, and the MIC values are recorded in Tables 7 and 8.

The results in Tables 2-6 demonstrate the marked superiority of Formulations 4 and 5 over Formulations 1, 2 and 3. In addition, the results in Tables 7 and 8, summarizing bacteriostatic activity, demonstrate that addition of the polymeric quaternary ammonium compound, which has bactericidal activity of its own, enhances the bacteriostatic activity of the 3-isothiazolones in a surprising manner; compare, for example, Formulations 1 and 2 with Formulation 4.

TABLE 2

Formulation 1 (Suspension Test)

| Test organism | Concentration in % | Contact time in min. | | | | | |
|---|---|---|---|---|---|---|---|
| | | 2½ | 5 | 15 | 30 | 60 | 120 |
| Staphylococcus aureus | 0.1 | + | + | + | + | — | — |
| | 0.2 | + | + | + | + | — | — |
| | 0.3 | + | + | + | + | — | — |
| Escherichia coli | 0.1 | + | + | + | + | + | + |
| | 0.2 | + | + | + | + | + | + |
| | 0.3 | + | + | + | + | + | — |
| Pseudomonas aeruginosa | 0.1 | + | + | + | + | + | — |
| | 0.2 | + | + | + | + | — | — |
| | 0.3 | + | + | + | — | — | — |
| Proteus vulgaris | 0.1 | + | + | + | + | + | — |
| | 0.2 | + | + | + | + | + | — |
| | 0.3 | + | + | + | + | — | — |

TABLE 3

Formulation 2 (Suspension Test)

| Test organism | Concentration in % | Contact time in min. | | | | | |
|---|---|---|---|---|---|---|---|
| | | 2½ | 5 | 15 | 30 | 60 | 120 |
| Staphylococcus aureus | 0.1 | + | + | + | + | + | + |
| | 0.2 | + | + | + | + | + | + |

TABLE 3-continued

Formulation 2 (Suspension Test)

| Test organism | Concentration in % | \multicolumn{6}{c}{Contact time in min.} |
|---|---|---|---|---|---|---|---|
| | | 2½ | 5 | 15 | 30 | 60 | 120 |
| Escherichia coli | 0.3 | + | + | + | + | + | + |
| | 0.1 | + | + | + | + | + | + |
| | 0.2 | + | + | + | + | + | + |
| | 0.3 | + | + | + | + | + | + |
| Pseudomonas aeruginosa | 0.1 | + | + | + | + | + | + |
| | 0.2 | + | + | + | + | + | + |
| | 0.3 | + | + | + | + | + | + |
| Proteus vulgaris | 0.1 | + | + | + | + | + | + |
| | 0.2 | + | + | + | + | + | + |
| | 0.3 | + | + | + | + | + | + |

TABLE 4

Formulation 3 (Suspension Test)

| Test organism | Concentration in % | 2½ | 5 | 15 | 30 | 60 | 120 |
|---|---|---|---|---|---|---|---|
| Staphylococcus aureus | 0.1 | + | + | + | + | + | + |
| | 0.2 | + | + | + | + | + | + |
| | 0.3 | + | + | + | + | + | + |
| Escherichia coli | 0.1 | + | + | + | + | + | + |
| | 0.2 | + | + | + | + | + | + |
| | 0.3 | + | + | + | + | + | + |
| Pseudomonas aeruginosa | 0.1 | + | + | + | + | + | + |
| | 0.2 | + | + | + | + | + | + |
| | 0.3 | + | + | + | + | + | + |
| Proteus vulgaris | 0.1 | + | + | + | + | + | + |
| | 0.2 | + | + | + | + | + | + |
| | 0.3 | + | + | + | + | + | + |

TABLE 5

Formulation 4 (Suspension Test)

| Test organism | Concentration in % | 2½ | 5 | 15 | 30 | 60 | 120 |
|---|---|---|---|---|---|---|---|
| Staphylococcus aureus | 0.1 | + | + | + | − | − | − |
| | 0.2 | + | + | − | − | − | − |
| | 0.3 | + | + | − | − | − | − |
| Escherichia coli | 0.1 | + | + | + | + | + | − |
| | 0.2 | + | + | + | + | − | − |
| | 0.3 | + | + | + | − | − | − |
| Pseudomonas aeruginosa | 0.1 | + | + | + | − | − | − |
| | 0.2 | + | + | − | − | − | − |
| | 0.3 | + | + | − | − | − | − |
| Proteus vulgaris | 0.1 | + | + | + | − | − | − |
| | 0.2 | + | + | + | − | − | − |
| | 0.3 | + | + | − | − | − | − |

TABLE 6

Formulation 5 (Suspension Test)

| Test organism | Concentration in % | 2½ | 5 | 15 | 30 | 60 | 120 |
|---|---|---|---|---|---|---|---|
| Staphylococcus aureus | 0.1 | + | + | + | − | − | − |
| | 0.2 | + | + | + | − | − | − |
| | 0.3 | + | + | − | − | − | − |
| Escherichia coli | 0.1 | + | + | + | + | + | + |
| | 0.2 | + | + | + | + | + | − |
| | 0.3 | + | + | + | − | − | − |
| Pseudomonas aeruginosa | 0.1 | + | + | + | + | − | − |
| | 0.2 | + | + | + | − | − | − |
| | 0.3 | + | + | − | − | − | − |
| Proteus vulgaris | 0.1 | + | + | + | + | − | − |
| | 0.2 | + | + | + | − | − | − |
| | 0.3 | + | + | − | − | − | − |

TABLE 7

MIC Value (Series dilution test)

| Formulation 1 | | Staphylococcus aureus | Escherichia coli | Pseudomonas aeruginosa | Proteus vulgaris |
|---|---|---|---|---|---|
| Concentration: (% by volume) | 1.0 | − | − | − | − |
| | 0.5 | − | − | − | − |
| | 0.25 | − | − | − | − |
| | 0.125 | + | + | + | + |
| | 0.1 | + | + | + | + |
| | 0.05 | + | + | + | + |
| | 0.025 | + | + | + | + |
| | 0.02 | + | + | + | + |
| | 0.01 | + | + | + | + |

| Formulation 2 | | Staphylococcus aureus | Escherichia coli | Pseudomonas aeruginosa | Proteus vulgaris |
|---|---|---|---|---|---|
| Concentration: (% by volume) | 1.0 | − | − | − | − |
| | 0.5 | − | − | − | − |
| | 0.25 | − | − | − | − |
| | 0.125 | − | − | − | − |
| | 0.1 | − | − | − | − |
| | 0.05 | − | − | − | − |
| | 0.025 | − | − | + | − |
| | 0.02 | − | − | + | + |
| | 0.01 | + | + | + | + |

| Formulation 3 | | Staphylococcus aureus | Escherichia coli | Pseudomonas aeruginosa | Proteus vulgaris |
|---|---|---|---|---|---|
| Concentration: (% by volume) | 1.0 | − | − | − | − |
| | 0.5 | − | − | − | − |
| | 0.25 | − | − | − | − |
| | 0.125 | − | − | − | − |
| | 0.1 | − | − | − | − |
| | 0.05 | − | − | + | − |
| | 0.025 | + | + | + | + |
| | 0.02 | + | + | + | + |
| | 0.01 | + | + | + | + |

TABLE 8

MIC Value (Series dilution test)

| Formulation 4 | | Staphylococcus aureus | Escherichia coli | Pseudomonas aeruginosa | Proteus vulgaris |
|---|---|---|---|---|---|
| Concentration: (% by volume) | 1.0 | − | − | − | − |
| | 0.5 | − | − | − | − |
| | 0.25 | − | − | − | − |
| | 0.125 | − | − | − | − |
| | 0.1 | − | − | − | − |
| | 0.05 | − | − | − | − |
| | 0.025 | − | − | − | − |
| | 0.02 | − | − | − | − |
| | 0.01 | − | − | + | − |

| Formulation 5 | | Staphylococcus aureus | Escherichia coli | Pseudomonas aeruginosa | Proteus vulgaris |
|---|---|---|---|---|---|
| Concentration: (% by volume) | 1.0 | − | − | − | − |
| | 0.5 | − | − | − | − |
| | 0.25 | − | − | − | − |
| | 0.125 | − | − | − | − |
| | 0.1 | − | − | − | − |
| | 0.05 | − | − | − | − |
| | 0.025 | − | − | + | − |
| | 0.02 | − | − | + | − |
| | 0.01 | + | + | + | + |

The practical significance of the synergistic composition of the invention, was demonstrated in an experiment in a hospital in 2 wash chambers of air conditioning systems over a period of 10 months. In this prolonged experiment, Formulation 4 exhibited superiority over known preparations used for this purpose. Its performance during the total time frame led to no criticism of any kind. The broad spectrum of activity at low concentrations and also at low temperatures, generally 14° to 16° C., is apparent from the data presented in Table 9 below. No instability was noted with respect to shearing forces or oxidation. Stabilization against hardness during the ten month experimental period also was demonstrated. Thus conventional 4-week cleaning cycles could be extended to 6–8 weeks. Troublesome deposits and scale formation were not observed. During the entire period of the experiment, no troublesome odor was noted in the equipment itself or in the air-conditioned rooms.

The acute oral toxicity of the formulation (observed over 14 days) of 12.14 ml/kg. in the rat is very low. According to the classification scheme of Hodge and Sterner into toxicity classes, the product is essentially non-toxic. Since the active components of the formulation do not evaporate to any significant extent, inhalation toxicity is very low. The formulation was essentially free of foaming in use.

TABLE 9

Practical experiments employing Formulation 4 in two wash chambers of hospital air-conditioning plants

| Elapsed Time (days) | Chamber 1 | | Chamber 2 | |
|---|---|---|---|---|
| | concentration (% by weight) | No. of organisms | concentration (% by weight) | No. of organisms |
| 0 | — | 9 × 10$^4$ | — | 6 × 10$^5$ |
| 6 | 0.60 | 0 | 0.21 | 4 × 10$^2$ |
| 9 | 0.65 | 0 | 0.67 | 0 |
| 16 | 0.58 | 0 | 0.52 | 0 |
| 22 | 0.30 | 0 | 0.59 | 0 |
| 37 | 0.31 | 7 | 0.13 | 6 |
| 43 | 0.57 | 2 | 0.54 | 1 |
| 57 | 0.64 | 0 | 0.73 | 0 |
| 69 | 0.07 | 0 | 0.24 | 0 |
| 79 | 0.28 | 0 | 0.32 | 0 |
| 92 | 0.07 | 0 | 0.15 | 0 |
| 115 | 0.04 | 0 | 0.17 | 0 |
| 128 | 0.13 | 0 | 0.14 | 0 |
| 139 | 0.18 | 0 | 0.16 | 0 |
| 157 | 0.19 | 0 | 0.16 | 0 |
| 175 | 0.11 | 0 | 0.18 | 0 |
| 191 | 0.11 | 0 | 0.18 | 0 |
| 206 | 0.25 | 0 | 0.28 | 0 |
| 219 | 0.37 | 0 | 0.17 | 0 |
| 237 | 0.34 | 0 | 0.21 | 0 |
| 258 | 0.30 | 0 | 0.26 | 3 |
| 280 | 0.26 | 0 | 0.26 | 0 |
| 293 | 0.36 | 0 | 0.35 | 0 |
| 307 | 0.25 | 0 | 0.36 | 0 |

We claim:
1. A synergistic bactericidal composition comprising in admixture
   (a) a mixture of polymeric quaternary ammonium compounds having the formula

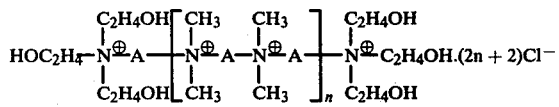

where A is —CH$_2$CH=CH—CH$_2$— and n is a number from 2 to 30; and
   (b) a mixture of 5-chloro-2-methyl-3-isothiazolone and 2-methyl-3-isothiazolone;
   wherein the ratio of component (a) to component (b) is about 1:1 to 2:1.
2. A method of protecting an aqueous system which is susceptible to contamination by deleterious bacteria from contamination by said bacteria which comprises treating the aqueous system with a bactericidally effective amount of the composition according to claim 1.

* * * * *